United States Patent [19]

Hollingshead

[11] 4,152,531

[45] May 1, 1979

[54] PROCESS OF PREPARING PHENOLIC COMPOSITIONS

[75] Inventor: William S. Hollingshead, Cuyahoga Falls, Ohio

[73] Assignee: The Goodyear Tire & Rubber Company, Akron, Ohio

[21] Appl. No.: 107,486

[22] Filed: Jan. 18, 1971

[51] Int. Cl.$^2$ ............................................. C07C 39/06
[52] U.S. Cl. .................................................. 568/793
[58] Field of Search ............... 260/624, 624 C, 624 R; 568/793

[56] References Cited

U.S. PATENT DOCUMENTS

| | | | |
|---|---|---|---|
| 2,975,216 | 3/1961 | Spacht | 260/624 C |
| 2,975,217 | 3/1961 | Spacht | 260/624 C |
| 3,035,015 | 5/1962 | Spacht | 260/624 R |

Primary Examiner—Werren B. Lone
Attorney, Agent, or Firm—J. A. Rozmajzl

[57] ABSTRACT

An improved process of preparing phenolic antioxidants in increased yields with superior color properties, the improvements being obtained by carefully controlling process variables such as the temperature of the reaction, moisture level and catalyst level.

15 Claims, No Drawings

PROCESS OF PREPARING PHENOLIC COMPOSITIONS

This invention relates to a process of preparing non-discoloring phenolic antioxidants. More particularly this invention relates to a process of preparing antioxidants in increased yields with good color properties.

Phenolic antioxidants of various types have found wide acceptance in the area of polymer stabilization. Preferred phenolic antioxidants are those which not only possess good antioxidant activity, but which also have a reduced tendency to discolor. Many processes are known in the art for preparing phenolic antioxidants. For obvious economic reasons processes which provide high yields of the phenolic product are quite desirable.

An object of the present invention is to provide a process for preparing certain phenolic antioxidants in high yields and with good color properties. Other objects and advantages will become apparent from the following description.

In accordance with the present invention, it has been found that the foregoing and additional objectives can be accomplished by a process of preparing phenolic antioxidants comprising reacting at least one phenolic reactant with at least one tertiary olefin having from 4 to 9 carbon atoms, in the presence of 8 to 40 parts by weight per mole of the phenolic reactant of at least one sulfonic acid catalyst wherein the phenolic reactant and catalyst together contain from 0.1 part to 2.0 parts by weight, or between 0 and 0.5 part by weight depending upon the olefin being used, of water per 100 parts by weight of phenolic compound plus catalyst.

The phenolic reactants that are used in the practice of the present invention are phenols having the following structural formula:

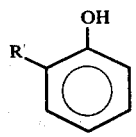

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms.

Preferably R is selected from the group consisting of hydrogen, methyl, ethyl, propyl, butyl, amyl, hexyl, heptyl, octyl and nonyl including not only the normal forms of the alkyl radicals, but also the secondary and tertiary forms of the alkyl radicals which are capable theoretically of being in such form. Also preferred are the phenolic reactants where R is selected from the group consisting of benzyl, alpha phenethyl, dimethyl benzyl and cyclohexyl.

The following are illustrative of the phenolic reactants used in the process of the present invention.
methyl
ethyl
n-propyl
isopropyl
n-butyl
sec.butyl
tert.butyl
n-amyl
sec.amyl
1,1-dimethyl propyl
n-hexyl
1,1-dimethyl butyl
1,1-dimethyl pentyl
cyclohexyl
1,1,3,3-tetramethyl butyl
benzyl
alpha phenethyl
dimethyl benzyl
nonyl
dodecyl
tetradecyl
hexadecyl
octadecyl Preferably the phenolic reactant is phenol or ortho cresol, and most preferably phenol.

Phenol and ortho cresol are commercially available compounds. The other ortho substituted phenolic reactants can be prepared according to the disclosures of U.S. Pat. No. 2,831,898.

The molar ratio of olefin to phenolic reactant can be varied. Where R is other than hydrogen and therefore the phenolic reactant is a monosubstituted phenol, the olefin to phenolic reactant molar ratio is at least about 1:1 and preferably at least 2:1. When R is hydrogen, i.e., when the phenolic reactant is phenol, the olefin/phenolic reactant molar ratio is at least 2:1, and preferably at least 3:1.

When the phenolic reactant is a monosubstituted phenol and the olefin is an olefin containing 4 to 7 carbon atoms or a mixture of such olefins, the olefin/phenolic reactant ratio is preferably from about 1:1 to about 3:1, more preferably from about 2:1 to about 3:1, and most preferably from about 2:1 to about 2.5:1. When the phenolic reactant is phenol and the olefin is an olefin containing 4 to 7 carbon atoms or a mixture of such olefins, the olefin/phenolic reactant molar ratio is preferably from about 2:1 to 4:1, more preferably from about 3:1 to about 4:1, and most preferably from about 3:1 to about 3.5:1.

When the phenolic reactant is a monosubstituted phenol and the olefin is an olefin containing 8 or 9 carbon atoms or a mixture of said olefins, the olefin/phenolic reactant molar ratio is preferably from about 1:1 to about 2:1, and most preferably from about 1:1 to about 1.5:1. When the phenolic reactant is phenol and the olefin is an olefin containing 8 or 9 carbon atoms or a mixture of said olefins, the olefin/phenolic reactant molar ratio is preferably from about 2:1 to about 3:1, and most preferably from about 2:1 to about 2.5:1.

Where an olefin containing 4 to 7 carbon atoms is used, the reaction is at least a two-step reaction. The initial step is a high temperature step and must take place at a temperature of from about 90° C. to about 140° C., preferably from about 125° C. to about 135° C. Where the phenolic reactant is phenol, from about 1 mole to about 2 moles of the olefin is added during the high temperature step. Where the phenolic reactant is a monosubstituted phenol, only the first mole is added in the high temperature step. In both cases at least one mole of the olefin is added subsequently in a low temperature step at a temperature of from about 10° C. to about 70° C., preferably from about 10° C. to about 60° C., and most preferably from about 25° C. to about 35° C. Preferably all of the remaining olefin in both cases is added in the low temperature step. Where the total olefin added is in excess of about two moles and the phenolic reactant is phenol, 0 to 1 mole of the olefin can be added in an intermediate step at a temperature of from about 10° C. to about 140° C. with the proviso that where the total amount of olefin added is less than 3 moles, the last mole is added in the low temperature step, and where the total olefin added is at least 3 moles, at least the third mole is added in the low temperature step. Preferably when the phenolic reactant is phenol, the first mole of the olefin is added in the high temperature step and the remainder of the phenol added in the low temperature step. Where the phenolic reactant is a monosubstituted phenol, no substantial amount of olefin is added in an intermediate step, at least the second mole of olefin being added in the low temperature step. Where the phenolic reactant is phenol and in excess of about 3 moles of olefin are added, or where the phenolic reactant is a monosubstituted phenol and in excess of 2 moles of olefin are added, preferably the excess portion is added at a temperature of from about 10° C. to about 140° C. although preferably the initial part of this excess portion, i.e., 0 to about 0.5 mole and even to about 1.0 mole is added in the low temperature step range.

Where an olefin containing 8 or 9 carbon atoms is used, the reaction is essentially a one-step reaction where all of the olefin is added within a temperature range of from about 50° C. to about 110° C., preferably from about 75° C. to about 85° C.

When it is desired to produce a trisubstituted phenolic reaction product, and an olefin containing 8 or 9 carbon atoms is used, preferably said olefin is used in a two-step reaction where said olefin is reacted in the first step and an olefin containing 4 to 7 carbon atoms is reacted in the second step.

When an olefin containing 8 or 9 carbon atoms is used in a two-step reaction where it is added in the first step, and an olefin containing 4 to 7 carbon atoms is added in the second step, the reaction temperature of the first step is from about 50° C. to about 110° C., preferably from about 75° C. to about 85° C., and the temperature of the second step is from about 10° C. to about 70° C., preferably from about 10° C. to about 60° C., most preferably from about 25° C. to about 35° C. When the phenolic reactant is phenol, the olefin containing 8 or 9 carbon atoms is added in an amount of from about 1 to about 2 moles per mole of phenol, preferably about 2 moles of olefin. The olefin containing 4 to 7 carbon atoms is added in an amount of from about 1 mole to about 3 moles, preferably about 1 mole to about 2.0 moles, most preferably from about 1 mole to about 1.5 moles, the total amount of olefin added being at least 2 moles and preferably from about 3 moles to 4 moles per mole of phenol. A particularly preferred embodiment of such a reaction is one where the olefin containing 8 or 9 carbon atoms is diisobutylene and the olefin containing 4 to 7 carbon atoms is isobutylene. Where the phenolic reactant is a monosubstituted phenol, i.e., R is other than hydrogen, the amount of olefin containing 8 or 9 carbon atoms is about 1 mole per mole of the phenolic reactant and the amount of olefin containing 4 to 7 carbon atoms is at least 1 mole and preferably from about 1 mole to 2 moles, the total amount of olefin being at least 2 moles and preferably from about 2 to 3 moles.

Higher levels of olefins than described earlier herein can be used, e.g., 10 moles of olefin per 1 mole of phenolic reactant and more. Although yield, based on the phenolic reactant charged, and color will not be substantially adversely affected by higher amounts of olefin, other undesirable results can occur.

Illustrative, but not limiting, of olefins which are used in the practice of the present invention are the following compounds.

isobutylene
2-methyl-1-butene
2,3-dimethyl-1-butene
2-methyl-1-pentene
2-methyl-2-pentene
diisobutylene
nonenes
cyclohexene
dodecene
tetradecene
1,1,3,3-tetramethyl butene-1

It is within the practice of the invention to perform the aforementioned reactions in the presence of reactions between other phenolic compounds (such as the reaction product of para cresol and dicyclopentadiene) and the tertiary olefin.

Mixtures of the phenolic reactants and mixtures of the olefins can be used within the practice of the present invention. It is only necessary that the process limitations described for the two classes of olefins are applied.

The practice of the present invention includes situations where one tertiary olefin of the present invention is reacted with a phenolic reactant within the practice of the present invention and the reaction product is further alkylated with another tertiary olefin of the present invention according to the teachings herein. One illustration is the two-step reaction described earlier herein where an olefin containing 8 or 9 carbon atoms is reacted with a phenolic reactant and then an olefin containing 4 to 7 carbon atoms is reacted with the product of the first reaction.

The reactions described herein can be batch, semi-continuous or continuous.

The sulfonic acids which can be used within the practice of the present invention as catalysts include aromatic sulfonic acids, such as toluene sulfonic acids, benzene sulfonic acid, xylene sulfonic acids, disulfonic acids of toluene, benzene, or xylenes; alkane sulfonic acids such as methane sulfonic acid, ethane sulfonic acid and propane sulfonic acids; cycloalkane sulfonic acids, such as cyclohexane sulfonic acid; and phenolic sulfonic acids such as phenol sulfonic acids, meta cresol sulfonic acids and ortho cresol sulfonic acids. The aromatic sulfonic acids can be prepared by sulfonation of an aromatic compound with oleum or sulfuric acid. The alkane sulfonic acids can be prepared by sulfonation of an alkane compound with oleum or by oxidation of mercaptans. The cycloalkane sulfonic acids can be prepared, at least in small amounts, by sulfonation of the cycloalkane with oleum. The phenolic sulfonic acids can be prepared by reacting a phenolic compound with sulfuric acid. In fact, sulfuric acid can be used as a "catalyst", since the sulfuric acid reacts with the phenolic reactant to form a phenol sulfonic acid. Mixtures of the sulfonic acids can also be used. The sulfonic acids include compounds having the following structural formulae:

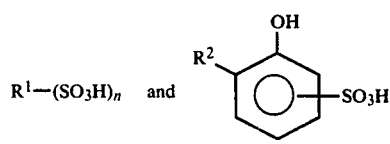

wherein $R^1$ is an organic radical, preferably a hydrocarbon radical having from 1 to 8 carbon atoms. $R^2$ is selected from the group consisting of hydrogen, alkyl groups having from 1 to 20 carbon atoms, cycloalkyl radicals having from 6 to 20 carbon atoms and aralkyl radicals having from 6 to 20 carbon atoms and wherein n is 1 or 2. Preferably —$SO_3H$ is in a position para to the hydroxyl group although it can be in a meta or ortho position. Preferably $R^1$ is phenyl, tolyl or dimethyl phenyl. Preferably $R^2$ is methyl.

Preferably the catalyst level is from about 16 to about 20 parts by weight per mole of the phenolic reactant.

Where the olefin contains 4 to 7 carbon atoms, the water level should be no greater than 0.5 part, i.e., between 0 and 0.5 part, preferably about 0.01 to about 0.5 part. However, where the olefin contains 8 or 9 carbon atoms, the water level is from about 0.1 part to about 2.0 parts by weight of water per 100 parts by weight of phenolic reactant plus catalyst, preferably about 1.0 part to about 1.2 parts.

It is well known that many phenolic antioxidant compositions, although they aid in preventing oxidative degradation, can cause discoloration of the organic environment, such as a polymer, to which it is added as a stabilizer. This has been referred to as tinting effect. In the past it has often been necessary to accept lower yields, that is to sacrifice yield, in order to obtain satisfactory color. It has been discovered that one method of obtaining certain phenolic antioxidants in high hields with a low tinting effect involves the process described herein where process variables such as the moisture level of the phenol and catalyst and the amount of catalyst used is carefully controlled. Naturally, optimum conditions will vary according to the particular phenol being alkylated and the olefin being used. However, if the guidelines described herein are followed one skilled in the art can easily obtain optimum results.

Polymers subject to deterioration by oxidation that can be conveniently protected by the antioxidants described herein include substituted and unsubstituted, saturated and unsaturated, natural and synthetic polymers. The oxidizable natural polymers of interest include natural rubber in its various forms, e.g., pale crepe and smoked sheet, and balata and gutta percha. The oxidizable synthetic polymers are prepared from a single monomer (homopolymer) or a mixture of two or more copolymerizable monomers (copolymers) wherein the monomers are combined in a random distribution or block form. The monomers may be substituted or unsubstituted and may possess one or more double bonds, for example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methyl-cyclooctene. Examples of vinyl monomers are styrene, acrylonitrile, acrylic acid, ethylacrylate, butylacrylate, methyl vinyl ether, vinyl acetate and vinyl pyridine. Examples of vinylidene monomers are $\alpha$-methylstyrene, methacrylic acid, methyl methacrylate, ethylmethacrylate, glycidyl methacrylate and vinylidene chloride. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

When added in free form normally 0.001 to 10.0 percent of the antioxidant by weight, i.e., parts by weight based on the weight of the polymer, i.e., 100 parts by weight of the polymer can be used, although the precise amount of the antioxidant which is to be employed will depend somewhat on the nature of the polymer and the severity of the deteriorating conditions to which the polymer is to be exposed. In unsaturated polymers such as those made from conjugated dienes, the amount of antioxidant necessary is greater than that required by a saturated polymer such as polyethylene. It has been found that an effective antioxidant amount of the disclosed stabilizers in rubbery unsaturated polymers will generally range from 0.05 to 5.0 parts by weight based on 100 parts by weight of the polymer, although it is commonly preferred to use from 0.5 to 3.0 parts by weight based on 100 parts by weight of the polymer. Mixtures of the age resisters may be used.

The following examples illustrate, but do not limit, the practice of the present invention.

EXAMPLES 1 to 14

Phenol was reacted with diisobutylene and isobutylene in the following amounts in Examples 1 to 14.

|  | Amount Parts by Weight |
| --- | --- |
| Phenol | 94 |
| Diisobutylene | 224 |
| Isobutylene | 56 |

Toluene sulfonic acid was used as the catalyst. The water content of the phenol and toluene sulfonic acid, the catalyst level and the temperature of the diisobutylene addition were varied as described in Table 1.

The following general procedure was used in Examples 1 through 14. The toluene sulfonic acid was added to the phenol and the water level adjusted to the amount indicated in Table 1. The diisobutylene was added over $3\frac{1}{2}$ hour period at the temperature indicated in the table and allowed to stir for 15 minutes after its addition was complete. The reaction mixture was cooled to 60° C. and the isobutylene added at 60° C.$\pm 2$° C. The catalyst was destroyed with aqueous $Na_2CO_3$ and the reaction mixture heated under vacuo to remove the volatiles, and filtered hot. Unstabilized SBR-1006 was stabilized by incorporating therein 1.0 part by weight of the antioxidants as 50 percent emulsions. The latex was then coagulated with salt and acid. One portion of each of the crumbs was dried in a gas fired oven. These 14 samples were given a visual color rating, the best being rated 1 and the poorest being given a rating of 14. A second portion of the web crumb was dried in an electric air oven. These samples were color rated visually as were the samples dried in the gas fired oven, from 1 to 14. Finally these samples which were dried in the electric air oven were passed 10 times through a cold mill and again visually evaluated for color and given a rating of from 1 to 14. The ratings were then totaled for each sample. The sample with the lowest total was rated 1, while the sample with the highest total was rated 14. These latter ratings are listed in Table 1.

Table I

| Example | Temperature of Diisobutylene Addition (°C.) | Percent Water on the Phenol | Toluene Sulfonic Acid (grams) | Yield (%) | Color Rating |
|---|---|---|---|---|---|
| 1 | 100 | 1.6 | 16 | 87.5 | 1 |
| 2 | 100 | 0.4 | 16 | 89.2 | 4 |
| 3 | 100 | 1.6 | 4 | 71.5 | 10 |
| 4 | 100 | 0.4 | 4 | 84.5 | 8 |
| 5 | 60 | 0.4 | 4 | 74.5 | 12 |
| 6 | 60 | 1.6 | 4 | 57.5 | 14 |
| 7 | 60 | 0.4 | 16 | 90.4 | 5 |
| 8 | 80 | 1.6 | 16 | 83.0 | 6 |
| 9 | 80 | 1.0 | 10 | 92.0 | 9 |
| 10 | 80 | 1.0 | 10 | 86.0 | 7 |
| 11 | 80 | 0.4 | 4 | 74.4 | 11 |
| 12 | 80 | 0.4 | 16 | 82.7 | 2 |
| 13 | 80 | 1.6 | 4 | 65.3 | 13 |
| 14 | 80 | 1.6 | 16 | 81.3 | 3 |

As the color data in Table I demonstrates, the examples illustrating the practice of the present invention, Examples 1, 2, 7, 8, 9, 10, 12 and 14, all possessed color properties superior to those of the examples illustrating products produced by processes outside the practice of the present invention, i.e., Examples 3, 4, 5, 6, 11 and 13, with one exception. The SBR containing the product of Example 4 was rated eighth, while the SBR containing the product of Example 9 was rated ninth. However, the latter compound was produced in a yield of 92.0 percent while the product of Example 4 was produced in a yield of 84.5 percent. Overall the data demonstrates that the process of the present invention not only results in high yields, but does so while maintaining good color properties. Preferably the isobutylene is added at a temperature of 25° C. to 35° C.

Example 15 illustrates the process of the present invention. In Example 15, the olefin is a propylene dimer, 2-methyl-1-pentene. Example 16 is an example outside the practice of the present invention, a major difference being that in Example 15 a portion of the propylene dimer was first added at a high temperature.

EXAMPLE 15

Forty-seven grams of phenol and 10 grams of toluene sulfonic acid were heated to 120° C. and 42 grams of 2-methyl-1-pentene added at 120° C. to 130° C. The reaction mixture was cooled to 40° C., and 105 grams more propylene dimer added at 40° C.±2° C. The catalyst was destroyed with aqueous sodium carbonate and the reaction mixture heated to 80° C. under vacuo to remove the volatiles and filtered. Incorporation of the product into unstabilized SBR-1006 latex as described above for Examples 1–14 yielded a light colored rubber.

EXAMPLE 16

Ninety-four grams of phenol and 12 grams of toluene sulfonic acid were heated to 40° C. and 200 grams of 2-methyl-1-pentene added over a period of 3 hours at 40° C.±2° C. The catalyst was destroyed with aqueous sodium carbonate and the reaction mixture heated under vacuo to 110° C. to remove the volatiles. Incorporation into unstabilized SBR-1006 latex as described above for Examples 1–14 yielded yellow rubber.

High yields were obtained in both Example 15 and Example 16. However, as indicated, the latter product was highly colored.

SBR polymers containing antioxidants prepared according to the practice of the present invention using phenol and 2-methyl-1-pentene and phenol and diisobutylene and isobutylene have actually been tested and found to possess good resistance to oxidation. In fact tests on any of the SBR-1006 polymers stabilized according to these working examples would demonstrate that all of the phenolic reaction products offered some degree of antioxidant protection to the polymers.

EXAMPLE 17

150 grams of 2-t-butyl phenol is substituted for the phenol in Example 15 to produce a light colored antioxidant composition in a high yield.

EXAMPLE 18

177 grams of 2-cyclohexyl phenol is substituted for the phenol in Example 15 to produce a light colored antioxidant composition in a high yield.

EXAMPLE 19

208 grams of 2-α-phenylethyl phenol is substituted for the phenol in Example 15 to produce a light colored antioxidant composition in a high yield.

EXAMPLE 20

16 grams of phenol sulfonic acid is substituted for the toluene sulfonic acid in Example 15 to produce a light colored antioxidant composition in a high yield.

EXAMPLE 21

9 grams of methane sulfonic acid is substituted for the toluene sulfonic acid in Example 15 to produce a light colored antioxidant composition in a high yield.

EXAMPLE 22

15 grams of cyclohexane sulfonic acid is substituted for the toluene sulfonic acid in Example 15 to produce a light colored antioxidant composition in a high yield.

EXAMPLE 23

235 grams of 2-methyl-1-butene is substituted for the propylene dimer to produce a light colored antioxidant composition in a high yield.

EXAMPLE 24

210 grams of 2-methyl-1-hexene is substituted for the propylene dimer to produce a light colored antioxidant composition in a high yield.

Any of the compounds of Examples 17 to 24 could be placed in a polymer SBR-1006 to produce a light colored polymer possessing improved resistance to oxidation.

As illustrated by the previous examples, any of the phenolic reactants, tertiary olefins and catalysts described herein can be used in the practice of the present invention if the requirements of catalyst levels, water levels, reaction temperatures and molar ratios are followed. Any oxidizable polymers including those specifically described earlier herein can be substituted for the SBR-1006 in the previous working examples to demonstrate the good color properties of the antioxidants produced by the process of the present invention. All of the compounds of the present invention would provide some degree of antioxidant protection to any of the said polymers.

While certain representative embodiments and details have been shown for the purpose of illustrating the invention, it will be apparent to those skilled in this art that various changes and modifications may be made therein without departing from the spirit or scope of the invention.

What is claimed is:

1. A process of preparing phenolic antioxidant compositions comprising reacting a combination comprising (A) one mole of at least one phenolic reactant having the following structural formula

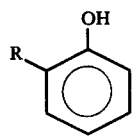

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms, with (B) at least one tertiary olefin having from 4 to 9 carbon atoms in the presence of 8 to 40 parts by weight of a catalyst consisting essentially of at least one sulfonic acid catalyst per mole of the phenolic reactant wherein (a) when R is hydrogen, the molar ratio of olefin to phenolic reactant is at least 2:1, (b) when R is other than hydrogen, the molar ratio of olefin to phenolic reactant is at least 1:1, (c) when the olefin contains 4 to 7 carbon atoms, the reaction is at least a two-step reaction the initial portion of the olefin being added in a high temperature step at a temperature of from 90° C. to 140° C., and a portion of the olefin being added subsequently in a low temperature step at a temperature of from 10° C. to 70° C. wherein when the phenolic reactant is phenol, 1 to 2 moles of the olefin are added during the high temperature step and at least one mole of the olefin is added subsequently in the low temperature step, with the proviso that where the total amount of olefin added is less than 3 moles, the last mole is added in the low temperature step, and where the total olefin added is at least 3 moles, at least the third mole is added in the low temperature step, and wherein when the phenolic reactant is a monosubstituted phenol the first mole of olefin is added in the high temperature step and the second mole of olefin is added in the low temperature step, (d) when the olefin contains 8 or 9 carbon atoms, the olefin is added at a temperature of from 50° C. to 110° C., (e) when the olefin contains 4 to 7 carbon atoms the water level is between 0 and 0.5 part of water per 100 parts by weight of phenolic reactant plus catalyst and (f) when the olefin contains 8 or 9 carbon atoms, the water level is from 0.1 part to 2.0 parts by weight of water per 100 parts by weight of phenolic reactant plus catalyst.

2. A two-step process of preparing phenolic antioxidant compositions comprising (1) reacting in the first step a composition comprising (A) one mole of at least one phenolic reactant having the following structural formula

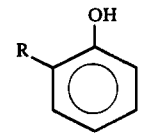

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms, with (B) at least one tertiary olefin having from 8 to 9 carbon atoms at a temperature of 50° C. to 110° C. in the presence of 8 to 40 parts by weight of a catalyst consisting essentially of at least one sulfonic acid catalyst per mole of the phenolic reactant the water level being from 0.1 part to 2.0 parts by weight of water per 100 parts by weight of phenolic reactant plus catalyst and (2) reacting in the second step the reaction product of the first step and at least one tertiary olefin having 4 to 7 carbon atoms at a temperature of 10° C. to 70° C. wherein (a) when the phenolic reactant is phenol the molar ratio of the olefin to the phenolic reactant in the first step is from 1:1 to 2:1 and the molar ratio of olefin in the second step to the original phenolic reactant is from 1:1 to 3:1 and (b) when R is other than hydrogen the molar ratio of the olefin to the phenolic reactant in the first step is 1:1 and the molar ratio of olefin in the second step to the original phenolic reactant is from 1:1 to 2:1.

3. The process according to claim 2 wherein the olefin containing 8 or 9 carbon atoms is 1,1,3,3-tetramethyl butene-1 and wherein the olefin containing 4 to 7 carbon atoms is isobutylene.

4. The process according to claim 3 wherein the phenolic reactant is phenol, the molar ratio of olefin to phenolic reactant in the first step is 2:1, the temperature in the first step is 75° C. to 85° C., the molar ratio of olefin to original phenolic reactant in the second step is 1:1 to 1.5:1 and the reaction temperature in the second step is from 25° C. to 35° C.

5. The process according to claim 1 wherein when the olefin contains 4 to 7 carbon atoms the molar ratio of olefin to phenolic reactant is from 2:1 to 4:1 when the phenolic reactant is phenol and 1:1 to 3:1 when R is other than hydrogen and wherein when the olefin contains 8 or 9 carbon atoms the molar ratio of olefin to phenolic reactant is 2:1 to 3:1 when the phenolic reactant is phenol and 1:1 to 2:1 when the R is other than hydrogen.

6. The process according to claim 1 wherein when the olefin contains 4 to 7 carbon atoms the molar ratio of olefin to phenolic reactant is from 3:1 to 4:1 when the phenolic reactant is phenol and 2:1 to 3:1 when R is other than hydrogen and wherein when the olefin contains 8 or 9 carbon atoms the molar ratio of olefin to phenolic reactant is 2:1 to 2.5:1 when the phenolic reactant is phenol and 1:1 to 1.5:1 when the R is other than hydrogen.

7. The process according to claim 6 wherein the olefin contains 4 to 9 carbon atoms and wherein when the olefin contains 4 to 7 carbon atoms the molar ratio of olefin to phenolic reactant is from 3:1 to 3.5:1 when the phenolic reactant is phenol and 2:1 to 2.5:1 when R is other than hydrogen.

8. The process according to claim 5 wherein the olefin contains 4 to 7 carbon atoms.

9. The process according to claim 5 wherein the phenolic reactant is selected from the group consisting of phenol and ortho cresol.

10. The process according to claim 5 wherein the phenolic reactant is 2-methyl-1-pentene.

11. The process according to claim 6 wherein the phenolic reactant is selected from the group consisting of phenol and ortho cresol and wherein the sulfonic acid catalyst is selected from the group consisting of aromatic sulfonic acids and alkane sulfonic acids.

12. The process according to claim 11 wherein the olefin contains 4 to 7 carbon atoms.

13. The process according to claim 11 wherein the olefin contains 8 or 9 carbon atoms.

14. The process according to claim 5 wherein the sulfonic acid is selected from the group consisting of aromatic sulfonic acids, alkane sulfonic acids and cycloalkane sulfonic acids.

15. The process according to claim 5 wherein the sulfonic acid is selected from the group consisting of aromatic sulfonic acids and alkane sulfonic acids.

* * * * *